(12) United States Patent
Blanco

(10) Patent No.: US 7,291,595 B2
(45) Date of Patent: Nov. 6, 2007

(54) USE OF ALPHA-1 ANTITRYPSIN FOR THE PREPARATION OF MEDICAMENTS FOR THE TREATMENT OF FIBROMYALGIA

(75) Inventor: Ignacio Blanco Blanco, Oviedo (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 10/549,759

(22) Filed: Sep. 19, 2005

(65) Prior Publication Data

US 2006/0084598 A1    Apr. 20, 2006

(30) Foreign Application Priority Data

Sep. 24, 2004  (ES) ............... 200402282

(51) Int. Cl.
*A61K 38/17*   (2006.01)
*C12N 9/76*    (2006.01)

(52) U.S. Cl. .......................... 514/12; 435/213

(58) Field of Classification Search ............. None
See application file for complete search history.

(56) References Cited

U.S. PATENT DOCUMENTS 4,440,679 A   4/1984  Fernandes et al.
6,737,405 B2  5/2004  Roemisch et al.

OTHER PUBLICATIONS

Stoller et al., Biochemical Efficacy and Safety of a New Pooled Human Plasma alpha-1 Antitrypsin, Respitin, Chest Journal, 2002, vol. 122, pp. 66-74.*

Juvelekian et al., Augmentation Therapy for alpha-1 Antitrypsin Deficiency, Drugs, Aug. 2004, vol. 64, vol. 15, pp. 1743-1756.*
Doring et al., Serine Proteinase Inhibitor Therapy in alpha-1 Antitrypsin Inhibitor Deficiency and Cystic Fibrosis, Pediatric Pulmonology, 1999, vol. 28, pp. 363-375.*
Blanco et al., "Alpha1-antitrypsin replacement therapy controls fibromyalgia symptoms in 2 patients with PI ZZ alpha1-antitrypsin deficiency," J Rheumatology 31(10):2082-2085, Oct. 2004.*
Alpha One International Registry (AIR) homepage, http://www.aatregistry.org/, printed on Aug. 18, 2006.*
Brantly M., *α1-Antitrypsin: Not Just an Antiprotease; Extending the Half-Life of a Natural Anti-Inflammatory Molecule by Conjugation with Polyethylene Glycol*, Am J Respir Cell Mol. Biol. (2002) 27:652-645.
Joaquin Esteve-Vives et al., *The Spanish Version of the Health Assessment Questionnaire: Reliability, Validity and Transcultural Eqivalency* Journal of Rheumatology (1993) 20:2116-2112.
Leonard R. Derogatis et al., *The SCL-90 and the MMPI: A Step in the Validation of a New Self-Report Scale*, Brit. J. Psychiat. (1976) 128:280-289.

* cited by examiner

*Primary Examiner*—Rebecca E. Prouty
*Assistant Examiner*—Rosanne Kosson
(74) *Attorney, Agent, or Firm*—Buchanan Ingersoll & Rooney PC

(57) ABSTRACT

The invention is based on the use of alpha-1 antitrypsin for the preparation of medicaments for the treatment of fibromyalgia, comprising the preparation of therapeutic concentrates of alpha-1 antitrypsin, in any form of administration tolerated by humans, the alpha-1 antitrypsin being obtained by purification of human plasma or being produced by recombinant or transgenic technology, with doses equal to or greater than 6 mg of alpha-1 antitrypsin per kg of body weight for a variable period of time.

12 Claims, No Drawings

USE OF ALPHA-1 ANTITRYPSIN FOR THE PREPARATION OF MEDICAMENTS FOR THE TREATMENT OF FIBROMYALGIA

This application claims priority to Spanish Application No. 200402282/5, filed on Sep. 24, 2004.

The present invention relates to the use of Alpha-1 antitrypsin (AAT) for the preparation of medicaments effective in the treatment of fibromyalgia (FM).

Fibromyalgia is a syndrome characterized by a clinical picture of chronic generalized musculoskeletal pain of non-articular origin. According to the classification criteria of the American College of Rheumatology (ACR) (Wolfe F et al. Arthritis Rheum 1990; 33: 160-248) the two basic characteristics for diagnosing fibromyalgia are the presence of generalized pain lasting more than three months and abnormal sensitivity to digital pressure, with a force of approximately 4 kg, at at least 11 out of 18 specific points called "tender points". In addition to pain, patients often present with other non-specific symptoms including fatigue aggravated by exertion, morning stiffness, sensations of tumefaction and morning stiffness in the hands, difficulty in getting to sleep and/or non-refreshing sleep, unexplained headaches, hypersensitivity to changes in temperature, anxiety, irritable colon, etc. These symptoms aid diagnosis but are not included in the diagnostic criteria. In addition, according to the ACR, the presence of a second disorder does not exclude the diagnosis of FM. The usual laboratory studies and imaging studies are generally negative or nonspecific in respect of FM.

The sociodemographic and clinical profile which appears in studies carried out on these patients shows that they are usually women (in 80-90% of cases) with an average age ranging from 35 to 60 years, with an average time of suffering from the problem of pain ranging from 6 to 12 years, and with a history of experiences of therapeutic failures in achieving relief from their symptoms.

Despite the rate of prevalence of the syndrome (from 1.5 to 3% of the population of Europe and North America) and the psychological and social cost associated with suffering from it, no clear conclusions have been reached either with regard to its aetiology or with regard to its pharmacological treatment.

Given the state of the art set out above, it is clear that there is a need to find medicaments effective in the treatment of fibromyalgia.

In order to achieve that aim, the inventor undertook wide-ranging in-depth investigations and tests which led to the present invention which is based on the use of Alpha-1 antitrypsin for the preparation of medicaments which have been found to be effective in the treatment of fibromyalgia.

Alpha-1 antitrypsin (AAT) is a glycoprotein secreted in hepatocytes and normally present in the serum and in the majority of tissues in high concentrations, where it acts as an inhibitor of serine proteases. Apart from its activity as an antiprotease, AAT could have an important antiinflammatory biological function since it has an outstanding inhibitory capacity in respect of many inflammation mediators and in respect of oxidant radicals (Brantly M. Am J Respir Cell Mol. Biol., 2002; 27: 652-654).

AAT deficiency is an hereditary disorder which causes chronic obstructive pulmonary disease (COPD), principally emphysema, in the early stages of adult life from 30-40 years. The second, more frequent, manifestation is the disease of the liver that can affect newborn babies, children and adults. Less frequent is an inflammatory disease of the skin called necrotizing panniculitis.

There are currently on the market therapeutic AAT preparations, normally obtained from human plasma, that have demonstrated the therapeutic usefulness thereof in the treatment of patients presenting with a deficiency of this protein.

In the course of the investigations and tests carried out by the inventor, he surprisingly found that Alpha-1 antitrypsin can be used for the preparation of medicaments effective in the treatment of fibromyalgia, achieving the total disappearance of the symptomatology caused by that disorder when the medicaments containing Alpha-1 antitrypsin (AAT) are infused periodically.

This finding is all the more surprising given that the novel therapeutic applications of the medicaments containing Alpha-1 antitrypsin could not in any way be connected with the known applications of AAT which were based strictly on compensating for the natural deficiency which manifested itself in the form of chronic obstructive pulmonary diseases (COPD) and inflammatory diseases of the skin in the form of panniculitis.

Without the inventor wishing to feel limited to any hypothesis in respect of the manner in which the novel medicaments containing AAT manifest themselves in the treatment of fibromyalgia, in non-limiting manner, he has established the hypothesis that AAT plays an important role in the control of the inflammatory component of the connective tissue of the skeletal member responsible for the induction of pain and the physical limitation caused by fibromyalgia.

In order to verify the effects, established experimentally, of the novel medicaments, the inventor carried out tests on humans, the details of which are set out in the following Examples.

EXAMPLES

Example 1

A female patient (patient 1) was diagnosed with FM: she presented with 18/18 tender points and met the requirements for the disorder, and other pathologies which could have a symptomatology similar to fibromyalgia were ruled out. This patient started therapy with intravenous infusions of AAT (60 mg/kg per week) and, surprisingly, after 2-3 infusions of AAT, she experienced a progressive control of the symptomatology caused by FM, which was maintained while alternative treatment with AAT was carried out. Subsequently, she received alternative therapy only for specific periods of time, the therapy being withdrawn between those periods of time. During the periods in which she did not receive therapy with AAT, a gradual recurrence of the symptoms associated with FM occurred, and there was a return to the basal situation at the end of 3-4 weeks after interrupting the treatment. When therapy with AAT was started again, the disappearance of the pain, the tiredness and the tender points occurred several times after 2-3 infusions of AAT.

Table 1 shows the levels of AAT (mg/dl) in the patient's serum, at its basal level, after the infusions of AAT, and before the next infusion.

Example 2

A female patient (patent 2) was diagnosed with FM: she presented with 13/18 tender points and met the requirements for the disorder, and other pathologies which could have a symptomatology similar to fibromyalgia were ruled out. This patient started therapy with intravenous infusions of AAT and, as in the previous case (Example 1), after 2-3 infusions of AAT, she experienced a progressive control of the symptomatology caused by FM which was maintained while alternative treatment with AAT was carried out. Subsequently, she received alternative therapy only intermittently for specific periods of time, the therapy being withdrawn between those periods of time. There was likewise a gradual recurrence of the symptoms associated with FM during the periods in which the patient was not receiving therapy with AAT. When the therapy was started again, the disappearance of the pain, the tiredness and the tender points was confirmed several times after 2-3 infusions of AAT.

Table 1 shows the levels of AAT (mg/dl) in the patient's serum, at its basal level, after the infusion of AAT, and before the next infusion.

Example 3

Female patient 3 had been suffering from very severe FM since the age of 35 (1984), and she was also suffering from slight bronchial asthma with normal pulmonary function. After an exhaustive study, it was proposed that she should receive compassionate treatment with commercial AAT and a placebo (8 doses of product: AAT, and the same number of doses of placebo: physiological serum with vitamin B) in order to test the effect of the treatment on her FM. After signing an informed consent, the treatment was started with weekly infusions of AAT (60 mg/kg/week, for 8 consecutive weeks). The patient initially presented with 18 tender points out of 18. From the start, a progressive improvement in the chronic pain and tiredness was observed and, from the $4^{th}$ dose of product, the disappearance of the 18 tender points together with a clear improvement in the clinical symptoms was observed. The patient, in the beginning, was incapable of carrying out the basic activities of daily life, such as washing herself or dressing, and required help from third parties to walk, etc. After the $4^{th}$ infusion, she recovered the lost functions again and the favourable situation was maintained while the product was infused into her (2 months). After the eighth dose, a switch was made to the infusion of placebo and after 10-12 days the patient experienced a clear reappearance of the generalized pain, and the reappearance of 18/18 tender points was observed. The questionnaires used to assess the impact of the process on the patient were the following: the Health Assessment Questionnaire, Spanish version (Esteve-Vives J, Battle-Gualda E, Reig A: Spanish Version of the Health Assessment Questionnaire: reliability, validity, and transcultural equivalency. J Rheumato 1993; 20: 2115-2122); the FIQ (relating to the impact of fibromyalgia on the quality of life); the Hamilton Depression Scale (with 17 items) and the SCL-90 (Derogatis L R, Rickels K, Rock. The SCL-90 and the MMPI: a step in the validation of a new self-report scale. Br J Psychiatry 1976; 128: 280-289).

Table 1 shows the levels of AAT (mg/dl) in the patient's serum, at its basal level, after the infusion of AAT, and before the next infusion.

TABLE 1

Levels of AAT (mg/dl) in the serum of the three patients, monitored in respect of its basal level, after the infusion of AAT, and before the next infusion (7 days).

|  | Basal AAT | AAT 24 h after infusion | AAT 7 days after infusion |
| --- | --- | --- | --- |
| Patient 1 | 43.8 ± 7.4 | 356.3 ± 39.9 | 71.0 ± 17.0 |
| Patient 2 | 40.3 ± 6.9 | 364.3 ± 13.7 | 103.8 ± 15.6 |
| Patient 3 | 93.1 ± 4.7 | 502 ± 43.5 | 209 ± 20.3 |

Each of patients 1, 2, and 3 responded to AAT treatment with a diminishment or elimination of the symptoms of fibromyalgia, e.g., generalized pain, tiredness, and tender points. The data of the Table demonstrate that patients 1 and 2 responded to a treatment regimen wherein the serum AAT levels were increased at least about 8-fold over basal levels at 24 hours following administration; whereas patient 3 experienced an increase of about 5-fold over basal levels. All three patients experienced about 100% increase in serum AAT over basal levels at 7 days following administration.

It has therefore been demonstrated that, by means of the present invention, it is found that patients with FM can be treated effectively with medicaments prepared on the basis of AAT. These patients were probably affected by a chronic inflammatory process of the soft tissues. This inflammatory process could be the result of an abnormal imbalance between biological proinflammatory products (cytokines, proteases and inflammatory mediators) and anti-inflammatory products (especially AAT). The initial factor or agent that would trigger the inflammation is unknown but it could be an infectious agent (for example HCV, HBV, Enterovirus, Borrelia burgdorferi, Mycoplasma sp, etc.) or an autoimmune process (for example, erythematous lupus, rheumatoid arthritis, etc.). These would cause an abnormal expression of inflammatory cytokines. Hitherto unknown genetic, environmental and possibly hormonal factors could be involved in the clinical expression of FM. The cytokines released at the subcutaneous connective tissue would attract circulating leukocytes to the inflammatory focus and would activate tissue macrophages and fibroblasts. The activated cells would release other cytokines, proteases and proinflammatory mediators which would normally be controlled by the natural anti-inflammatories (especially AAT). However, if the load of the inflammatory mediators overcomes the anti-inflammatory defences (by excessive production), an imbalance would be generated which would promote the development of an inflammation. This inflammatory process would stimulate the nocireceptors of the skin which would send stimuli to the brain, and the stimulated cortex would generate a sensation of generalized pain. On the other hand, by the efferent reflex pathway, the nerve discharges would cause generalized spasm of the skeletal muscle and vasospasm which would be expressed in muscular fatigue and hyperalgesia. The remaining symptoms of FM would result from those principal events.

The treatment of FM can be carried out with therapeutic concentrates of AAT which are purified from human plasma or produced by recombinant or transgenic technology. Likewise, treatment is possible with plasma or other therapeutic products that contain a sufficient amount of AAT to achieve a minimum dose.

As happens with other proteins, to obtain the expected effect, it would not necessarily be necessary the presence of the complete Alpha-1 antitrypsin molecule. Therefore, for the treatment of FM, they might be useful molecules having a partial sequence of amino acids derived from the corresponding sequence of the Alpha-1 antitrypsin molecule. These molecules can be obtained by synthetic methods or by transgenic or recombinant technology.

For this treatment, it is reckoned that a dose equal to or greater than 6 mg of AAT/kg infused with a periodicity of from 3 to 31 days is sufficient. A preferred dosage of AAT is from 15 to 360 mg/kg infused with a periodicity of from 3 to 31 days. A more preferred dosage is from 25 to 60 mg/kg each week or multiples of these amounts adjusted in function of the interval of time foreseen until the next dose, in a proportional manner.

The present invention further provides a method of treating fibromyalgia comprising administering to a patient suffering from, or at risk of developing, fibromyalgia a therapeutically effective amount of AAT in combination with one or more pharmaceutically inert carriers. Other embodiments involve the administration of at least about 6 mg/kg patient body mass. Depending on various factors, including the severity of the symptoms, the AAT can be administered in quantities of about 15 to about 360 mg/kg. In one embodiment, AAT is administered in quantities of between 25 and 60 mg/kg every week or multiples of these quantities adjusted according to the time interval foreseen until the next dose, in a proportional manner.

The treatment regimen of the invention includes repeated periodic administration of AAT to effect a diminishment or elimination of the symptoms of fibromyalgia. One embodiment involves administration of AAT every 3 to 31 days. Another embodiment involves repeated administration of AAT every 7 to 21 days.

More particularly, the treatment regimens of the instant invention comprise administration of about 15 to about 360 mg AAT/kg patient body mass and repeating the administration at about 3 to 31 days. Another treatment regimen comprises administration of between 25 and 60 mg/kg each week or multiples of these quantities adjusted according to the time interval foreseen until the next dose, in a proportional manner.

Alternatively, an effective treatment regimen can be constructed to achieve a desired serum AAT level (mg/dl). For example, the data show that improvement in fibromyalgia symptoms is observed when sufficient AAT is administered to increase serum AAT level by about 100% over basal level at about 7 days following infusion. Thus, another embodiment involves a treatment regimen comprising administration of sufficient AAT to a symptomatic patient suffering from fibromyalgia as will increase the patient's AAT level by about 100% at about 7 days following administration and repeating the administration at least once at about 3 to about 31 days. Another such embodiment involves administration of sufficient AAT to a symptomatic patient suffering from fibromyalgia as will increase the patient's AAT level by about 100% at about 7 days following administration and repeating the administration at least once at about 7 to about 21 days.

Similarly treatment regimens have been effective wherein AAT is administered to increase serum AAT levels about 5-fold over basal levels at 24 hours following administration. Thus, the present invention further affords a method of treatment comprising administering to a patient suffering from fibromyalgia a quantity of AAT as will produce serum AAT levels at least about 5-fold greater than basal levels at 24 hours following administration. Optionally, the administration is repeated one or more times at intervals of about 3 to 31 days; and may be repeated at intervals of about 7 to 21 days. In another embodiment, AAT is administered to increase serum AAT levels at least about 8-fold over basal levels at 24 hours following administration.

In one embodiment, the AAT is administered by parenteral injection. When administered parenterally, the AAT is compounded as a solution or suspension in a pharmaceutically acceptable vehicle or carrier. Examples of suitable vehicles include: Water For Injection, Sterile Water For Injection, and other aqueous vehicles (e.g., sodium chloride injection, Ringer's injection, dextrose injection, dextrose and sodium chloride injection, and lactated Ringer's injection); water-miscible vehicles (e.g., ethyl alcohol, polyethylene alcohol, propylene glycol); and nonaqueous vehicles (e.g., corn oil, cottonseed oil, peanut oil, and sesame oil). The need for and selection of other excipients, preservatives, buffers, biocides, and the like are within the skill of the ordinary practitioner and will depend on various factors including the route of administration, desired shelf-life, and storage and shipping conditions.

Additionally, other processing steps can be employed that preserve, protect, or disinfect antitrypsin formulations. See, e.g., U.S. Pat. No. 6,737,405 (describing stabilized preparations of, e.g., antitrypsin, that can be pasteurized without loss of action or denaturation); and U.S. Pat. No. 4,440,679 (describing protein pasteurization method), both of which are incorporated herein by reference.

The invention claimed is:

1. A method of treating a patient diagnosed with fibromyalgia comprising administering to the patient about 15 to about 360 mg of alpha-1-antitrypsin per kg patient body mass, and repeating the administration at least once with a periodicity of between 3 and 31 days.

2. The method of claim 1, wherein alpha-1-antitrypsin is administered at a dose of between 25 and 60 mg/kg per week.

3. A method of treatment comprising administering sufficient alpha-1-antitrypsin to a patient diagnosed with fibromyalgia as will increase the patient's alpha-1-antitrypsin level by about 100% over basal level at about 7 days following administration and repeating the administration at least once at about 3 to 31 days.

4. The method of claim 3, wherein the administration of alpha-1-antitrypsin is repeated at least once at about 7 to 21 days.

5. A method of treating a patient diagnosed with fibromyalgia comprising administering to the patient a quantity of alpha-1-antitrypsin as will increase serum alpha-1-antitrypsin levels to about 5-fold greater than basal levels at 24 hours following administration.

6. The method of claim 5, wherein the administration is repeated one or more times at about 3 to 31 days.

7. The method of claim 5, wherein the administration is repeated one or more times at about 7 to 21 days.

8. The method of claim 5, wherein a quantity of alpha-1-antitrypsin is administered as will increase serum alpha-1-antitrypsin levels about 8-fold over basal levels at 24 hours following administration, and the administration is repeated one or more times at about 7 to 21 days.

9. A method of treating a patient diagnosed with fibromyalgia comprising administering to said patient by parenteral infusion about 15 to 360 mg alpha-1-antitrypsin per kg patient body mass, and repeating said infusion at least once at 3 to 31 days to effect a diminishment of the symptoms of fibromyalgia in said patient.

10. The method of claim 9, wherein the dose of alpha-1-antitrypsin is between 25 and 60 mg of alpha-1-antitrypsin/kg body mass, and the infusion is repeated at least once at about 7 to 21 days.

11. The method of claim 9, wherein the administration is carried out by intravenous infusion.

12. The method of claim 9, wherein the administration is carried out by intravenous infusion and the dose of alpha-1-antitrypsin is between 25 and 60 mg of alpha-1-antitrypsin/kg body mass, and the infusion is repeated at least once at about 7 to 21 days.

* * * * *